United States Patent [19]

Makari

[11] 4,297,338

[45] Oct. 27, 1981

[54] MALIGNANT TUMOR IMMUNITY LEVEL DETECTION

[76] Inventor: Jack G. Makari, 88 Everett Rd., Demarest, N.J. 07627

[21] Appl. No.: 186,781

[22] Filed: Sep. 12, 1980

Related U.S. Application Data

[63] Continuation-in-part of Ser. No. 14,827, Feb. 26, 1979, abandoned, which is a continuation-in-part of Ser. No. 920,258, Jun. 29, 1978, abandoned, which is a continuation of Ser. No. 679,926, Apr. 26, 1976, abandoned, which is a continuation-in-part of Ser. No. 342,097, Mar. 16, 1973, abandoned, which is a continuation-in-part of Ser. No. 37,406, May 11, 1970, abandoned, which is a continuation of Ser. No. 421,683, Dec. 28, 1964, abandoned, which is a continuation-in-part of Ser. No. 75,454, Aug. 26, 1959, abandoned, and a continuation-in-part of Ser. No. 31,855, May 1, 1970, abandoned, which is a continuation of Ser. No. 530,774, Mar. 1, 1966, abandoned, which is a continuation-in-part of Ser. No. 127,849, Jul. 31, 1961, abandoned, which is a continuation-in-part of Ser. No. 75,454, Aug. 26, 1959, abandoned, and a continuation-in-part of Ser. No. 159,473, Jul. 2, 1971, abandoned, which is a continuation-in-part of Ser. No. 535,364, Mar. 18, 1966, abandoned, which is a continuation-in-part of Ser. No. 421,683, Dec. 28, 1964, abandoned.

[51] Int. Cl.$^3$ .................... A61K 49/00; A61K 39/00
[52] U.S. Cl. ......................................... 424/9; 424/12
[58] Field of Search ....................................... 424/9, 12

[56] References Cited

FOREIGN PATENT DOCUMENTS 906819 9/1962 United Kingdom .................... 424/9

OTHER PUBLICATIONS

*Brit. Med. Journal*, Aug. 9, 1958, pp. 355–361, Makari.
*Chem. Abstracts*, vol. 47, 11479, 1953.

*Primary Examiner*—Frederick E. Waddell
*Attorney, Agent, or Firm*—Darby & Darby

[57] ABSTRACT

Disclosed is a method of detecting in a human the subject's extent of immunity to malignant tumor development, by (a) intradermally injecting into the subject an aqueous isotonic diagnostic solution of (i) a polysaccharide-like antigenic product obtained by rupturing the cells of malignant tumor tissue as by disintegration in hypertonic aqueous saline solution, removing and discarding the nuclear and cell wall fractions, separating from the residual liquid the mitochondrial fraction by a treatment including centrifugation, removing from that fraction lipid and protein materials, and dialyzing the remainder against isotonic phosphate saline solution, or (ii) the produce derived from the chromatographically treating the former product and combining selected fractions of an eluate, and (b) measuring separately the two longest diameters perpendicular to one another of the erythema produced at the injection site, and (c) calculating their average and from its value determining the level of immunity from a respective value level of immunity scale. How the respective polysaccharide-like antigenic products are obtained also is disclosed.

6 Claims, No Drawings

MALIGNANT TUMOR IMMUNITY LEVEL DETECTION

This application is (i) a continuation-in-part of my copending application Ser. No. 14,827 filed Feb. 26, 1979, now abandoned, as a continuation-in-part of my then copending (now abandoned) application Ser. No. 920,258 filed June 29, 1978 as a continuation of my then copending (now abandoned) application Ser. No. 679,926 filed Apr. 26, 1976 as a continuation-in-part of my then copending application (now abandoned) Ser. No. 342,097 filed Mar. 16, 1973, as a continuation-in-part of my then pending (now abandoned) application Ser. No. 37,406 filed May 11, 1970, which is a continuation of my then pending (now abandoned) application Ser. No. 421,683 filed Dec. 28, 1964 and which is a continuation-in-part of my then copending but now abandoned application Ser. No. 75,454 filed Aug. 26, 1959; (ii) and a continuation-in-part of my then pending application Ser. No. 31,855 filed May 1, 1970 (now abandoned) as a continuation of my then pending application Ser. No. 530,774 filed Mar. 1, 1966 (now abandoned) as a continuation-in-part of my then pending but now abandoned application Ser. No. 127,849 filed July 31, 1961 which in turn was a continuation-in-part of my then pending but now abandoned application Ser. No. 75,454; and (iii) Ser. No. 159,473 filed July 2, 1971 (now abandoned) as a continuation-in-part of my then pending but now abandoned application Ser. No. 535,364 filed Mar. 18, 1966 as a continuation-in-part of the aforesaid application Ser. No. 421,683.

This invention is that of a method of detecting in a human subject the level or extent of the subject's immunity against malignant tumor occurrence or development, by (a) intradermally injecting into the subject an isotonic diagnostic solution (i) of the polysaccharide-like antigenic product obtained by rupturing malignant tumor tissue cells, removing and discarding the nuclear and cell wall fractions, separating from the residual liquid the mitochondrial fraction by a treatment involving centrifugation, removing from that fraction lipids and also protein until protein-free, dialyzing the remainder, for example, against isotonic phosphate saline solution to remove dialyzable inorganic salts, followed by further treatment described below or (ii) of the antigenic product derived from chromatographic treatment of the foregoing antigenic product and combining selected fractions of that treatment; and (b) measuring separately the two longest diameters perpendicular to one another of any erythema developed at the injection site, and (c) calculating their mean (i.e. average of those two diameters, and from the magnitude of the resulting mean determining the level of immunity from a scale presented on page 6 below.

With the high rank held by cancer in annual deaths, any diagnostic agent which the physician can use by ordinary intradermal injection to obtain an indication of the level of the human patient's immunity to malignant tumor (i.e. cancer) should be a valuable tool in the physician's armamentarium of tests. Such a test can fit in well with the general overall physical examination especially with the patient in the cancer age group (i.e. those at least 40 years old).

Moreover, such diagnostic agent can be particularly useful in a general physical or other examination of a patient who, for example, is a smoker, or whose employment exposes him to a carcinogenic environment. Thus, the indication of an undesirably low level of immunity by such a test may well influence the physician in advising the patient on the need to change his smoking scale or as to seeking a desirable change in type or location of employment.

In response to accumulation of tumor polysaccharide-like sensitizing substances or antigens (referred to hereinafter briefly as TPS), the host's system resorts to protective measures related to general resistance, such as production of resistance factor-antibody inhibitor, properdin, interferon, nucleases, and other substances. Properties related to specific immunity are also mobilized by the host against the tumor polysaccharide-like antigens that by now have accumulated at the site of irritated cells behaving like an "endogenous homograft".

In response to this TPS-coated "endogenous homograft", the host produces protective antibodies (believed to be formed by the lymphocyte reticuloendothelial system) that tend to neutralize the reactive sites on the TPS antigens and thus to render the TPS nonantigenic. In addition, cell-mediated immune responses (such as those produced by lymphocytes) also are considered to be significant in host tumor inter-action. The result is a state of immunity. However, as the body ages and encounters daily insult, the degree of immunity tends to decrease and susceptibility to cancer tends to increase.

The method of the invention is detecting the extent or level of immunity to the inception of malignant tumor in a human subject, by (a) intradermally injecting into the subject to be tested a level of immunity-detecting effective dosage of an isotonic aqueous saline diagnostic dispersion containing essentially (i) a glycoprotein-polysaccharide-like antigenic substance (briefly designated as GPAS) of apparently glycoprotein nature, derived from cancer tissue and which readily disperses, and is stable, in cold to boiling water and in aqueous saline (usually sodium chloride, sometimes potassium chloride) solutions, is non-dialyzable at a cutoff point of 3500 from water, inert to alkali and to phosphate buffered isotonic saline solutions, precipitated from aqueous media by isopropanol and insoluble in it, ether, chloroform, and butanol, withstands autoclaving at 250° F. and at 16 lbs. per square inch for at least 30 minutes and retains its activity after autoclaving even for 6 hours, gives a positive Molisch test (described by Kabat and Meyer in "Experimental Immunochemistry" pages 315–317) and a negative Dische test, and on acid hydrolysis followed by de-ionization, as with dilute sulfuric acid or by heating it in a 2 N aqueous solution of trifluoroacetic acid or in contact with the acid form of a polystyrene nuclear-sulfonic acid cation exchange resin in a sealed tube in a boiling water bath for 24 hours, yields a hydrolysate containing identifiable sugars and on finite analysis shows trace amounts of various amino acids typical of N-glycoproteins; or (ii) an improved glycoprotein-polysaccharide-like antigenic substance (briefly called IGPAS) derived from the GPAS by lyophilizing it, fractionating the lyophilizate dissolved in a compatible buffered aqueous solution by gel fractionation to obtain, by eluting the content of the fractionation column, fractions falling within a selected range, and subjecting the individual fractions to ultraviolet examination to exclude those fractions lacking protein and/or polysaccharide containing substances; and which glycoprotein-polysaccharide-like antigenic substance dispersed in an isotonic aqueous saline solution in an amount for it to contain, for example, 0.25 micrograms (i.e. gamma) of it per milliliter, and thereafter one-tenth milliliter of the resulting solution is injected intradermally into a human subject to be tested, can produce about the injection site an erythema, (b) measuring separately the two longest diameters perpendicular to one another of any erythema developed at the injection site, and (c) calculating the mean of those two diameters and from the magnitude of the resulting mean determining the level of immunity.

Each of these two diameters measured is an overall diameter i.e. of the bleb (the mild swelling usually produced about an injection site) plus the annular ring of erythema about the bleb. Then, the bleb alone with no, or at most with little, erythema up to the mean (of the two diameters) being 10 mm. indicates no immunity. A mean of from over 10 to 15 millimeters (mm.) indicates minimum immunity, of 16 to 20 mm. indicates moderate immunity, of over 20 to 30 mm. indicates good immumity, and over 30 to 50 or more indicates what can be said to be best immunity.

The foregoing glycoprotein-polysaccharide-like antigen can be derived from any human malignant tumor tissue, for example, by disintegrating any of the human malignant, i.e. cancerous, tumor tissues such as carcinoma, fibrosarcoma, lymphoma, and melanoma tissues as by grinding and/or homogenizing, as by sonic vibrations, to rupture the cell walls, removing the cell walls and nuclei to provide the mitochondrial fraction of the cells as by differential centrifugation, removing from a saline suspension of that fraction its lipids and protein, and isolating the glycoprotein-polysaccharide-like antigen (briefly called GPAS) from the rest by any available compatible method for separating polysaccharides (two of which are described further below).

More specifically the glycoprotein-polysaccharide-like antigen is obtained, for example, by the following procedure:

Human malignant tumor tissue, such as carcinoma, fibrosarcoma, lymphoma, and melanoma, obtained by resection from a suitable source (a human harboring such malignant tumor), for example, lung carcinoma, is disintegrated by grinding, or advantageously homogenizing it, in 0.2 N (N is normal) aqueous saline solution to provide a suitably centrifugable homogenate of from 15 to 50% solids by weight, optimally of about 20%. The homogenate is centrifuged at a sufficient speed for a practical time, for example, from about 1000 to about 3500 r.p.m., and as far as presently indicated optimally about 3000 r.p.m., for about 2 to about 30 minutes and beneficially from about 15 to 20 minutes, to throw down the cell walls and nuclei. That sediment is discarded.

The supernatant liquid is centrifuged at from about 9500 to about 15,000, and optimally at about 10,000, r.p.m., for from about 10 to about 30 minutes to cause sedimentation of the mitochondrial fraction. This sedimentation can be conducted at any temperature below that at which enzymatic action occurs, and for example, between about zero and 25°, and optimally from zero to about 5° C.

The latter sediment containing the mitochondrial fraction preferably is washed (say, once or twice) by being agitated in isotonic sodium chloride solution and each time similarly sedimented, and then is dispersed back to its original volume (of its initial centrifugation) in aqueous sodium or potassium chloride solution, advantageously 0.15 normal, and the glycoprotein-polysaccharide-like antigenic substance then is derived from the dispersion by any applicable available procedure to remove polysaccharides, for example:

(i) The dispersion is mixed with from about 0.5 to 5 times its volume, and optimally in about equal volumes, with a compatible organic lipid solvent, e.g. diethyl ether, and with vigorous stirring, for a sufficient time of at least a few minutes to dissolve the lipids, for example, from about 5 to about 10 minutes. The mixture then is allowed to stand for a sufficient time to separate into its ether and aqueous phases. The ether layer is discarded.

Aqueous alkali is added to the drawn off aqueous phase to raise its pH to above 7 and the temperature is raised to from about 80° C. to boiling, with occasional stirring, and for a time sufficient to hydrolyze the alkali hydrolyzable proteins, as can be observed, if necessary, by simple known test. Thus, sodium hydroxide solution is admixed to the aqueous phase in an amount to provide alkali corresponding to from about 10 to about 15% by volume calculated as 2 N NaOH, and their mixture is heated on a water bath at 100° C. for about 30 minutes.

The hydrolysis mixture then is cooled and dialyzed for a sufficient time, in practice about 2 hours, at a conveniently safe temperature, as from zero to about 25° C. and optimally at from above freezing to about 5° C., against distilled water or advantageously a phosphate buffered aqueous sodium or potassium chloride solution [e.g. at pH 6.8 and composed of 0.81 g. (i.e. gram) $Na_2HPO_4$, 1.04 g. $KH_2PO_4$, 6.8 g. NaCl, and 1 liter distilled water] to remove the so dialyzable products of this foregoing hydrolysis.

The dialysis residue comprising the active skin testing substance is shaken in from about 0.5 to about 5 volumes, and optimally about equal volumes, of a protein-denaturizing agent, for example, chloroform, wherein the protein and polysaccharide-like antigenic substance is insoluble, and for a sufficient time from about 15 to 45 minutes, optimally about 20 minutes, whereby the denatured protein collects at the interface between the chloroform and aqueous layers while the mixture is permitted to separate into these respective layers, advantageously by centrifugation at a speed, sufficient to expedite phase separation, of about 1000 r.p.m. or less to about 2000 r.p.m., for about 10 to 30 minutes. The denatured protein at the interface and the heavier chloroform layer is discarded. This deproteination is repeated until no further denatured protein occurs at the interface.

The relatively clear aqueous phase contains the desired glycoprotein-polysaccharide-like antigen (the GPAS), in this case in the amount of about 180 gamma per ml., and having the properties recited above (p. 4 line 22 to p. 5 line 12). The GPAS product so derived from lung carcinoma has a specific optical rotation in aqueous acid of $(a)_D - 30°$.

(ii) Alternate polysaccharide separation: An effective alternate method for isolating the glycoprotein-polysaccharide-like antigen involves suspending the sediment from the centrifugation of the mitochondrial fraction in a compatible aqueous medium such as acetate buffer, of 157.5 g. of $NaC_2H_3O_2.3H_2O$ in 3 liters of distilled water, and adjusting the pH to about 6 with a compatible acid, e.g. glacial acetic acid. This suspension is ground at about 0° C., preferably slowly to avoid undue temperature rise. It may even be frozen and thus ground and thereafter heated merely enough to melt the frozen suspension. The thawed ground suspension then is centrifuged at a speed of at least about 10,000, and better between about 15,000 to about 20,000 r.p.m.

The supernatant is withdrawn and the sediment discarded. Several volumes of a water-miscible precipitant for polysaccharides, e.g. about 5 volumes of cold isopropanol, are admixed with the supernatant to precipitate the lipid-free glycoprotein-polysaccharide-like antigenic substance. The precipitate is separated (e.g., by the above acetate buffer and their mixture similarly ground as above) and suspended in a compatible aqueous medium. The resulting suspension is centrifuged as before, and the supernatant likewise precipitated with isopropyl alcohol.

This precipitate is dissolved in cold distilled water and the resulting turbid greenish solution is deproteinized by compatible deproteinization such as the Sevag method, Biochemische Zeitschrift, volume 273 (1934) page 319. Thus, 50 ml. of chloroform and 10 ml. of butyl alcohol are added for each 150 ml. of precipitate solution, and their mixture is agitated in a homogenizer at about 3° C. The resulting emulsion is broken into its phases as by centrifugation, and the aqueous layer is separated.

This aqueous layer then is adjusted to a concentration of 3% sodium acetate with saturated sodium acetate solution and brought to pH 6 with acetic acid. One-half volume of cold isopropyl alcohol is added to precipitate the glycoprotein-polysaccharide-like antigenic substance, and the suspension is left overnight. This Sevag procedure is repeated until the product is completely deproteinized as earlier above described. The desired GPAS then is recovered by centrifugation to break the emulsion, from which is separated the aqueous phase which contains the GPAS.

Treating the hydrolysates to convert their carbohydrates to their per(trimethylsilylated)methylglycosides, followed by gas chromatography found the following identifiable sugars and related products: fucose, galactose, glucose, mannose, xylose, N-acetylglucosamine and N-acetylneuraminic acid.

Amino acids found in the acid hydrolysates are glutamic acid, methionine, aspartic acid, leucine, alanine, valine, proline, lysine, phenylalanine, serine, isoleucine, tyrosine, arginine, histidine, ornithine, cysteine and glycine.

The indicated content preponderance of the protein component (apparently not subject to the alkali hydrolysis) of the glycoprotein-polysaccharide-like antigen enables referring to the GPAS as a glycoprotein. The GPAS is characterized as being polysaccharide-like because it appears that its polysaccharide moiety dominates its effectiveness after its injection.

The method thus enables detecting the level of immunity to the inception of a malignant tumor by administering an inception-detecting effective dosage of the GPAS, for example, in an injection-suitable dilution of the end product, (e.g. obtained at the end of the first above disclosed polysaccharide separation step, [subdivision (i) above] said to contain about 180 gamma of the GPAS per milliliter of that product.

That liquid product used in a malignant tumor inception-detecting effective dosage, preferably diluted with isotonic saline (usually sodium chloride although possibly also potassium chloride) solution (say, in the range of 1 part of the GPAS liquid to about 1 to about 2000 or even more, and preferably at a dilution of 1 part of that GPAS to from about 800 to about 1200 of isotonic saline solution) and on injecting 0.1 milliliter of the selected dilution, by the mean of the two longest diameters perpendicular to one another of the resulting erythema about the injection site reveals the extent of immunity to inception of a malignant tumor.

The greater the mean of the two longest diameters perpendicular to one another of the erythema measured in from about 0.5 to about 5 minutes and preferably from about 1 to 2.5 minutes after the injection, the greater the level of immunity. Epidemiologic studies on volunteers classified by ages have shown that (i) the highest level of immunity occurs in the younger age groups (e.g. up to about 14 years of age) and (ii) the immunity declines and appears at a minimum in the subjects at ages 40 to 49 years (considered the cancer age group).

Interestingly, a further similar study with these same volunteers showed that on repeating the same test solution injection to each of them 2 weeks after the first injection revealed an anamnestic type of immunologic response in that the erythema produced by this later test injection manifested an increase in magnitude of the results over those of the first test injection. That then indicates the capacity of the GPAS antigen to stimulate immune response by apparently enhancing immunity.

The method of the invention can be conducted by using the GPAS antigen prepared not only from the earlier above specifically named carcinoma, fibrosarcoma, lymphoma, or melanoma tissue but also with GPAS similarly obtained by the earlier above described procedure from malignant tissue taken from any of the same or other malignant tumors found in any of the organs of the human body, in which malignant tumors occur.

Illustrative of such other malignant tumors, but without being restricted to them, are breast carcinoma, abdominal lymphoma, ovarian adenocarcinoma, adenosarcoma, melanotic melanoma, cancer of the pancreas (such as at the head of it), myeloma, mesothelioma, adenoid carcinoma, alveolar cancer, cyctic carcinoma, dendritic cancer (patilloma), dermoid cancer, encephaloma, endothelioma, epidermal cancer, hematoid carcinoma, medullary cancer, acinous carcinoma, epidermoid carcinoma, mucinous carcinoma, aquamous carcinoma, odontogenic fibrosarcoma, giant follicular lymphoma, lymphoblastoma, and lymphocytoma, as well as malignant tumors that may occur in any other organ such as in a muscle, the stomach, intestines, colon, bladder, rectum, or others.

The combination of steps described in the earlier above disclosed method of obtaining the GPAS antigenic substance from lung carcinoma can be considered as separately respectively repeated, as if written out in full herein, with tissue from each of these other just above named illustrative malignant tumors as further examples, without repeating each one separately to make this disclosure prolix.

The expression "saline suspension" as used herein is intended as an aqueous suspension as in an aqueous solution of the applicable alkali metal chloride, most usually sodium chloride, although possibly even potassium chloride (as in such countries as Germany whose potassium chloride costs less than sodium chloride) and in any suitable concentration, if not earlier above specifically recited, for in the above instances where concentration specifically is recited or indicated by the type of operation, it may even be concentrated or saturated.

Similarly, the expression "saline solution" or "aqueous saline solution" is intended to be the same as said for the saline solution referred to in the just preceding explanation. By "isotonic saline" is intended the well known isotonic saline solution containing from about 0.75 to 0.9 percent of sodium chloride, as commonly used in pharmaceutical chemistry for aqueous injectable preparations. In countries as in Germany where potassium chloride may cost less than sodium chloride and the frequency of administration is not so great as to provoke any concern as to upsetting the potassium balance, potassium chloride also may be used for the isotonic saline solution.

The alkali hydrolysis of proteins described at page 8 lines 9 to 17 above is not restricted to using sodium hydroxide as the alkali. Any other alkali compatible (in the sense of inert to the polysaccharide moiety of the GPAS) can be used to provide the alkaline hydrolysis condition, such as potassium hydroxide of any other suitable compatible alkali which will not produce in the hydrolysate any water-insoluble product or one which would not be dialyzable in the dialysis step that follows.

Also, the vehicle against which the dialysis is to be conducted is not restricted to the phosphate buffered alkali metal chloride solution used in the dialysis described at page 7 lines 18 to 26, for any other compatible suitable aqueous dialysis solution or even distilled water can be used.

While the invention has been explained by detailed description of certain specific embodiments of it, it is understand that various substitutions and modifications can be made in it within the scope of the appended claims which are intended also to cover equivalents of the disclosed best mode embodiment.

What is claimed is:

1. The method of detecting the level of immunity to the development of a malignant tumor in a human subject, which method comprises the combination of steps of
    (a) intradermally injecting into the subject to be tested a level of immunity to malignant tumor development detecting effective dosage of a diagnostic isotonic aqueous sodium or potassium chloride solution containing essentially a glycoprotein-polysaccharide-like antigenic substance derived from malignant tumor tissue and which readily disperses in cold to boiling water and in aqueous sodium or potassium chloride solutions to a stable, non-dialyzable solution, is stable to boiling in water and in aqueous sodium or potassium chloride solutions, is non-dialyzable at a cutoff point of 3500 from water, inert to alkali and to phosphate buffered isotonic aqueous sodium or potassium chloride solutions, precipitated from aqueous media by isopropanol and insoluble in it, ether, chloroform, and butanol, withstands autoclaving at 250° F. and 16 lbs. per square inch pressure for at least 30 minutes and retains its activity after autoclaving even up to 6 hours, gives a positive Molisch test and a negative Dische test, and on acid hydrolysis as by heating it in a 2 N aqueous solution of trifluoroacetic acid or in contact with the acid form of polystyrene nuclear-sulfonic acid cation exchange resin, in a sealed tube in a boiling water bath for 24 hours, yields a hydrolysate containing identifiable sugars and on finite analysis shows also trace amounts of various amino acids typical of N-glycoprotein; and which glycoprotein-polysaccharide-like antigenic substance when dispersed in an isotonic aqueous sodium or potassium chloride solution in an amount for it to contain about 0.25 micrograms of said antigenic substance per milliliter and thereafter one-tenth milliliter of the resulting solution is injected intradermally into a human subject to be tested, produces an erythema about the injection site;
    (b) measuring separately the two longest diameters perpendicular to one another of the resulting injection-produced bleb and any erythema encircling it, and
    (c) calculating the mean of those two diameters and from the magnitude of the mean determining the level of immunity from a scale, on which a mean of 10 mm. or less indicates no immunity and a mean of at least from over 10 to 15 mm. indicates minimum immunity and a mean of 30 to 50 mm. or more indicates best immunity.

2. The method of claim 1, wherein said glycoprotein-polysaccharide-like antigen is derived by a procedure comprising disintegrating malignant tumor tissue obtained from a malignant tumor in a human subject, to rupture the cell walls of said tissue, removing and discarding the nuclear and cell wall fraction of said disintegrated tissue, separating the mitochondrial fraction from the residue after removal of said nuclear and cell wall fraction, removing lipids and protein from said mitochondrial fraction, and dialyzing said lipid-free mitochondrial fraction against water or isotonic aqueous phosphate buffered sodium or potassium chloride solution to remove substances thus dialyzable from said lipid-free mitochondrical fraction.

3. The method as claimed in claim 2, wherein said tumor tissue is carcinoma, fibrosarcoma, lymphoma, or melanoma tissue.

4. The method as claimed in claim 2, wherein said tissue is disintegrated in an aqueous sodium or potassium chloride solution containing a sufficient concentration of said chloride to rupture the cell walls of said tissue.

5. The method as claimed in claim 4, wherein said tumor tissue is from about 15 to about 50 percent by weight of its mixture with the aqueous solution.

6. The method of claim 5, wherein the mitochondrial fraction is removed from said aqueous mixture of disintegrated tissue by a treatment including centrifuging said mixture at about 10,000 r.p.m., removing the lipids by extraction of said fraction with a compatible organic lipid solvent; and said lipid-free fraction is heated at a temperature of from about 80° C. to boiling at a pH above 7 for a time sufficient to hydrolyze alkali hydrolyzable proteins.

* * * * *

UNITED STATES PATENT AND TRADEMARK OFFICE
CERTIFICATE OF CORRECTION

PATENT NO. : 4,297,338
DATED : Oct. 27, 1981
INVENTOR(S) : Jack G. Makari

It is certified that error appears in the above-identified patent and that said Letters Patent are hereby corrected as shown below:

In the Abstract:

Line 13, change "produce" to --product--.

Column 1, line 53, change "diameters," to --diameters),--.

Signed and Sealed this

Twenty-third Day of February 1982

[SEAL]

Attest:

GERALD J. MOSSINGHOFF

Attesting Officer

Commissioner of Patents and Trademarks